(12) United States Patent
Ko et al.

(10) Patent No.: US 9,492,078 B2
(45) Date of Patent: Nov. 15, 2016

(54) EXTENDED RANGE IMAGING

(71) Applicant: Optovue, Inc., Fremont, CA (US)

(72) Inventors: Tony H. Ko, San Jose, CA (US);
Yonghua Zhao, Fremont, CA (US);
David Huang, South Pasadena, CA (US)

(73) Assignee: OPTOVUE, INC., Fremont, CA (US)

( * ) Notice: Subject to any disclaimer, the term of this patent is extended or adjusted under 35 U.S.C. 154(b) by 0 days.

(21) Appl. No.: 14/101,253

(22) Filed: Dec. 9, 2013

(65) Prior Publication Data

US 2014/0160430 A1    Jun. 12, 2014

Related U.S. Application Data

(62) Division of application No. 12/506,766, filed on Jul. 21, 2009, now Pat. No. 8,605,287.

(60) Provisional application No. 61/135,613, filed on Jul. 21, 2008.

(51) Int. Cl.
*G01B 9/02* (2006.01)
*A61B 3/10* (2006.01)
(Continued)

(52) U.S. Cl.
CPC .............. *A61B 3/102* (2013.01); *A61B 3/0025* (2013.01); *A61B 5/0066* (2013.01);
(Continued)

(58) Field of Classification Search
CPC  A61B 3/0025; A61B 5/0066; A61B 5/0073; A61B 5/7257; G01B 9/02004; G01B 9/0201; G01B 9/02021; G01B 9/02028; G01B 9/02044; G01B 9/02091
USPC ................................................. 356/479, 497
See application file for complete search history.

(56) References Cited

U.S. PATENT DOCUMENTS 5,301,010 A * 4/1994 Jones et al. .................... 356/479
6,198,540 B1 * 3/2001 Ueda et al. .................... 356/479
(Continued)

FOREIGN PATENT DOCUMENTS

JP      10-267830 A      10/1998
JP      2003-172690 A    6/2003
(Continued)

OTHER PUBLICATIONS

M. Wojtkowski, R. Leitgeb, A. Kowalczyk, T. Bajraszewski, and A.F. Fercher, "In vivo human retinal imaging by Fourier domain optical coherence tomography", J. Biomed. Opt. 7, 457-463 (2002).
(Continued)

*Primary Examiner* — Tarifur Chowdhury
*Assistant Examiner* — Jonathon Cook
(74) *Attorney, Agent, or Firm* — Haynes & Boone, LLP

(57) ABSTRACT

An imager that can provide separated images corresponding to differing depths in a sample is presented. In accordance with some embodiments of the invention, an imager can include a light source; a sample arm that receives light from the light source, directs the light to a sample, and captures light returning from the sample; a modulation source that provides different modulations corresponding to differing imaging depths in the sample; a detector system to receive the captured light from the sample with the different modulations; and a processor that receives signals from the detector system and separates a plurality of images corresponding with the differing image depths in the sample.

13 Claims, 13 Drawing Sheets

(51) Int. Cl.
*A61B 5/00* (2006.01)
*A61B 3/00* (2006.01)

(52) U.S. Cl.
CPC .......... *A61B 5/0073* (2013.01); *G01B 9/0201* (2013.01); *G01B 9/02004* (2013.01); *G01B 9/02021* (2013.01); *G01B 9/02028* (2013.01); *G01B 9/02044* (2013.01); *G01B 9/02091* (2013.01); *A61B 5/7257* (2013.01)

(56) References Cited

U.S. PATENT DOCUMENTS

| | | | |
|---|---|---|---|
| 6,256,102 | B1 | 7/2001 | Dogariu |
| 6,628,747 | B1 | 9/2003 | Schotland et al. |
| 6,775,007 | B2 | 8/2004 | Izatt et al. |
| 7,139,079 | B2 | 11/2006 | Lindner |
| 7,336,366 | B2 | 2/2008 | Choma et al. |
| 7,348,563 | B2 | 3/2008 | Fujita |
| 7,400,410 | B2 | 7/2008 | Baker et al. |
| 2002/0085208 | A1* | 7/2002 | Hauger .................. G01D 5/268 356/479 |
| 2005/0174578 | A1 | 8/2005 | Wei |
| 2005/0254061 | A1 | 11/2005 | Alphonse |
| 2006/0100528 | A1 | 5/2006 | Chan et al. |
| 2006/0232783 | A1 | 10/2006 | Choma et al. |
| 2007/0252999 | A1* | 11/2007 | Hogan .......................... 356/450 |
| 2008/0112603 | A1 | 5/2008 | Boyden et al. |
| 2008/0170225 | A1* | 7/2008 | de Boer et al. ............... 356/327 |

FOREIGN PATENT DOCUMENTS

| | | |
|---|---|---|
| TW | 200532169 A | 10/2005 |
| WO | WO 01/42735 A1 | 6/2001 |
| WO | WO 02/071042 A2 | 9/2002 |
| WO | WO 03/007811 A2 | 1/2003 |
| WO | WO 2006/028926 A1 | 3/2006 |

OTHER PUBLICATIONS

M. Wojtkowski, A. Kowalczyk, R. Leitgeb, and A.F. Fercher, "Full range complex spectral optical coherence tomography technique in eye imaging", Opt. Lett. 27, 1415-1417 (2002).

J.F. de Boer, B. Cense, B.H. Park, M.C. Pierce, G.J. Tearney, and B.E. Bouma, "Improved signal-to-noise ratio in spectral-domain compared with time-domain optical coherence tomography", Opt. Lett. 28, 2067-2069 (2003).

R. Leitgeb, C.K. Hizenberger, and A.F. Fercher, "Performance of fourier domain vs. time domain optical coherence tomography," Opt. Express 11, 889-894 (2003).

M.A. Choma, M.V. Sarunic, C.H. Yang, and J.A. Izatt, "Sensitivity advantage of swept source and Fourier domain optical coherence tomography", Opt. Express 11, 2183-2189 (2003).

D. Huang, Y. Li, and S. Radhakrishnan, "Optical coherence tomography of the anterior segment of the eye", Ophthalmology Clin. N. Am. 17, 1-6 (2004).

Y. Yasuno, S. Makita, T. Endo, G. Aoki, M. Itoh, and T. Yatagai, "Simultaneous B-M-mode scanning method for real-time full-range Fourier domain optical coherence tomography", Appl. Opt. 45, 1861-1865 (2006).

R.K. Wang, "In vivo full range complex Fourier domain optical coherence tomography", Appl. Phys. Lett. 90, 054103 (2007).

Baumann et al (Full range complex spectral domain optical coherence tomography without additional phase shifters, Oct. 2007, vol. 15, No. 20, Optics Express).

B. Grajciar, M. Pircher, C.K. Hitzenberger, O. Findl, and A.F. Fercher, "High sensitive measurement of the human axial eye length in vivo with Fourier domain low coherence interferometry", Opt. Express 16, 2405-2414 (2008).

PCT International Search Report and the Written Opinion mailed Sep. 9, 2009, in related international Application No. PCT/US2009/051263.

International Preliminary Report on Patentability and Written Opinion for related PCT Application No. PCT/US2009/051263, dated Jan. 25, 2011.

First Office Action in related Chinese Application No. 200980128730.7, dated Apr. 26, 2012.

2$^{nd}$ Office Action from related Chinese Office Action dated Dec. 4, 2012, from related Chinese Patent Application No. 200980128730.7, 3 pages.

Supplemental European Search Report dated May 23, 2013, from related European Patent Application No. 09800879.0, 6 pages.

Notice of Reasons for Rejection mailed Aug. 6, 2013, in related Japanese Application No. 2011-520135.

First Office Action mailed Sep. 3, 2014, in related Taiwanese Application No. 098124643.

* cited by examiner

EXTENDED RANGE IMAGING

CROSS-REFERENCE TO RELATED APPLICATIONS

This application relates to and claims priority to U.S. Provisional Patent Application No. 61/135,613 filed Jul. 21, 2008, the disclosure of which is incorporated herein by reference, as if fully stated here, for all purposes. This application is a divisional application of U.S. patent application Ser. No. 12/506,766, filed on Jul. 21, 2009, which is hereby incorporated by reference in its entirety.

BACKGROUND

1. Field of Invention

The present disclosure is directed to systems for biomedical imaging and ranging, and more specifically to methods and systems associated with optical coherence tomography (OCT) imaging and low coherence interferometry (LCI).

2. Discussion of Related Art

Optical coherence tomography (OCT) is a two-dimensional imaging modality based on low coherence interferometry (LCI) principles. OCT has been used for non-invasive human eye retinal imaging for many years. Great interest has also been shown in the use of OCT to image anterior chamber as well as perform axial eye length measurements for refractive, cataract, and glaucoma surgical planning. See D. Huang, Y. Li, and S. Radhakrishnan, "Optical coherence tomography of the anterior segment of the eye," Opthalmology Clin. N. Am. 17, 1-6 (2004).

However, imaging the entire anterior chamber of the eye remains challenging due to the limited scan depth of typical OCT techniques. The depth of the anterior chamber is very long compare to that of the retina. Average depth from cornea to crystalline lens is about 3.5 mm. Typically, anterior segment OCT scan depth should be about 5-6 mm. If the posterior capsule of the crystalline needs to be imaged, the depth of the image should be at least 9 to 10 mm. If the entire eye length is to be measured, the scan depth should be more than 30 mm. In performing axial eye length measurements, only two low coherence interferometry (LCI) measurements acquired from the front and back surfaces of the eye are typically utilized. However, the eye is likely to move in the axial direction between the two measurements at the two surfaces, thereby decreasing the accuracy of the eye length measurements.

Therefore, a need exists for a method that can simultaneously acquire multiple OCT images spanning multiple axial ranges in order to perform imaging and/or measurements over large scan ranges.

SUMMARY

In accordance with some embodiments of the present invention, an imager can include a light source; a sample arm that receives light from the light source, directs the light to a sample, and captures light returning from the sample; a modulation source that provides different modulations corresponding to differing imaging depths in the sample; a detector system to receive the captured light from the sample with the different modulations; and a processor that receives signals from the detector system and separates a plurality of images corresponding with the differing image depths in the sample.

In some embodiments, the modulation source includes a reference arm with a plurality of reference paths. In some embodiments, each reference path includes a mirror and a modulator coupled to the mirror, and wherein a path length of the reference path correlates with the image depth of one of the plurality of images. In some embodiments, the imager may further include a splitter/coupler coupled to the light source, the sample arm, the reference arm, and the detection system, wherein the splitter/coupler provides light to the sample arm and the reference arm, receives light from the sample arm and the reference arm, and provides combined light from the sample arm and the reference arm to the detector system.

In some embodiments, the modulation source includes an interferometer coupled between the light source and a light coupler, the light coupler providing light to the sample arm from the interferometer and to the detector system from the sample arm. In some embodiments, the light coupler can be a splitter/coupler. In some embodiments, the light coupler can be a circulator.

In some embodiments, the modulator system includes an interferometer, and further including a splitter/coupler that receives light from the light source, provides the light to the sample arm and the interferometer, combines light received from the sample arm and the interferometer, and provides light to the detector system.

In some embodiments, the modulation source includes a first reflector and a second reflector, and further includes a splitter/coupler coupled to receive light from the light source and provide light to the first reflector and the second reflector of the modulation source, the splitter/coupler also receiving light from the first reflector and the second reflector and provide combined light; and a light coupler coupled to receive the combined light from the splitter/coupler, couple light to the sample arm, and direct light received from the sample arm to the detector system.

In some embodiments, the processor executes instructions to acquire a combined dataset with the OCT imager having a plurality of images; perform a transform on the combined dataset to form a frequency distribution; spectrally separate the frequency distribution into a plurality of separated data based on a modulation frequency of each of the plurality of separated data; and perform mathematical operations on each of the plurality of separated data to generate separate images.

These and other embodiments are further discussed below with respect to the following Figures.

FIGURES

Figure 9A:
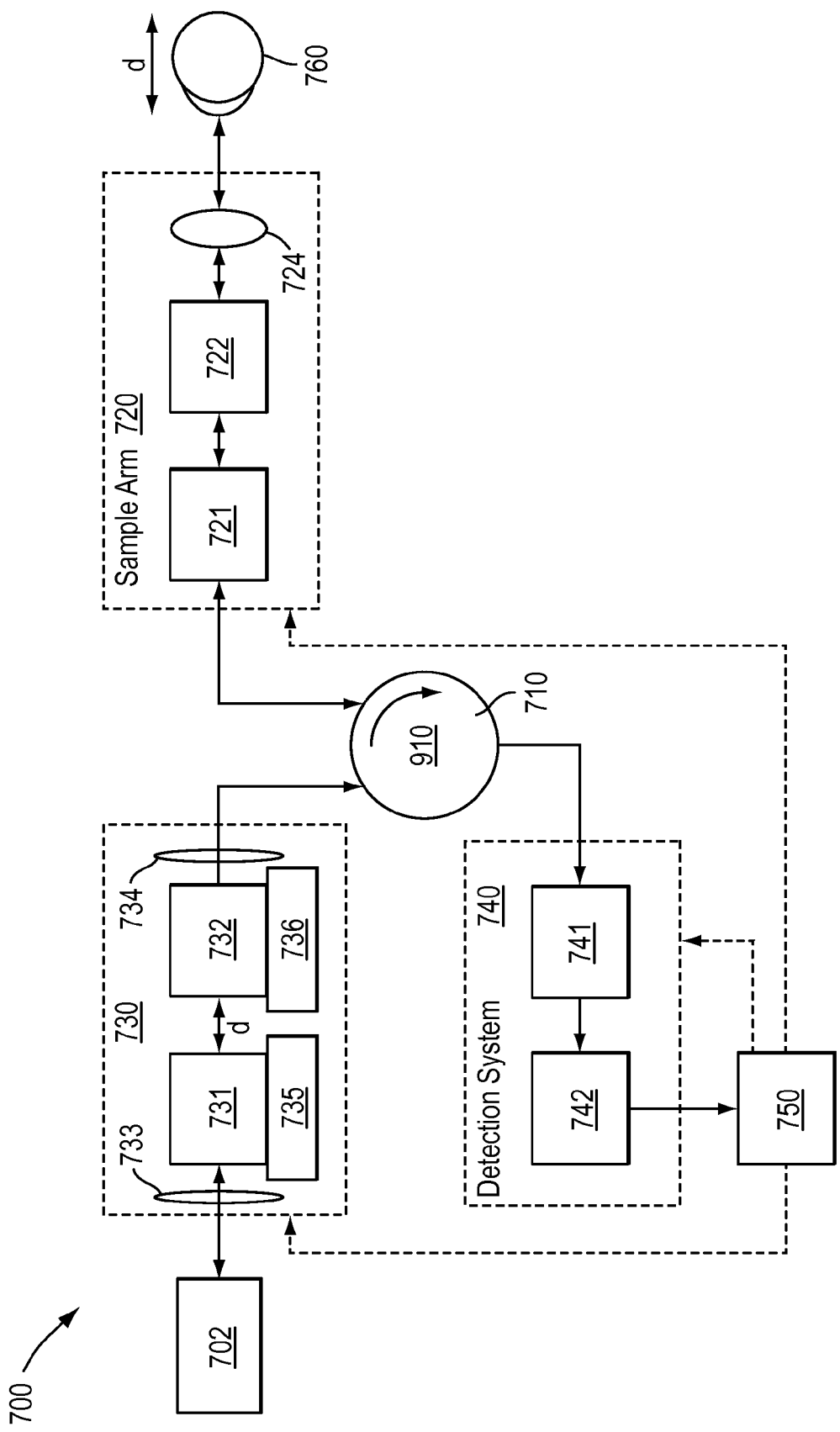
Figure 9B:
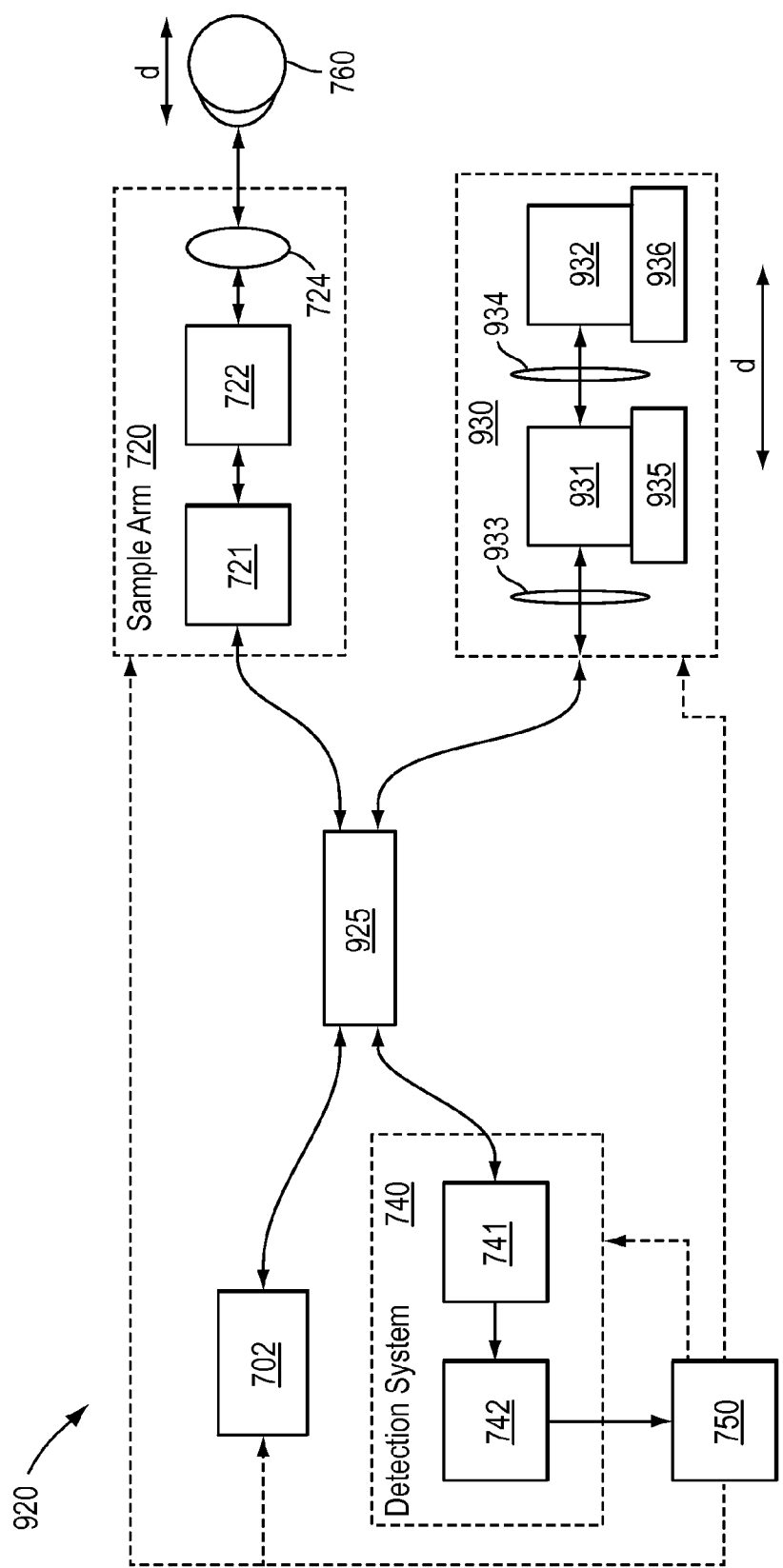
Figure 9C:
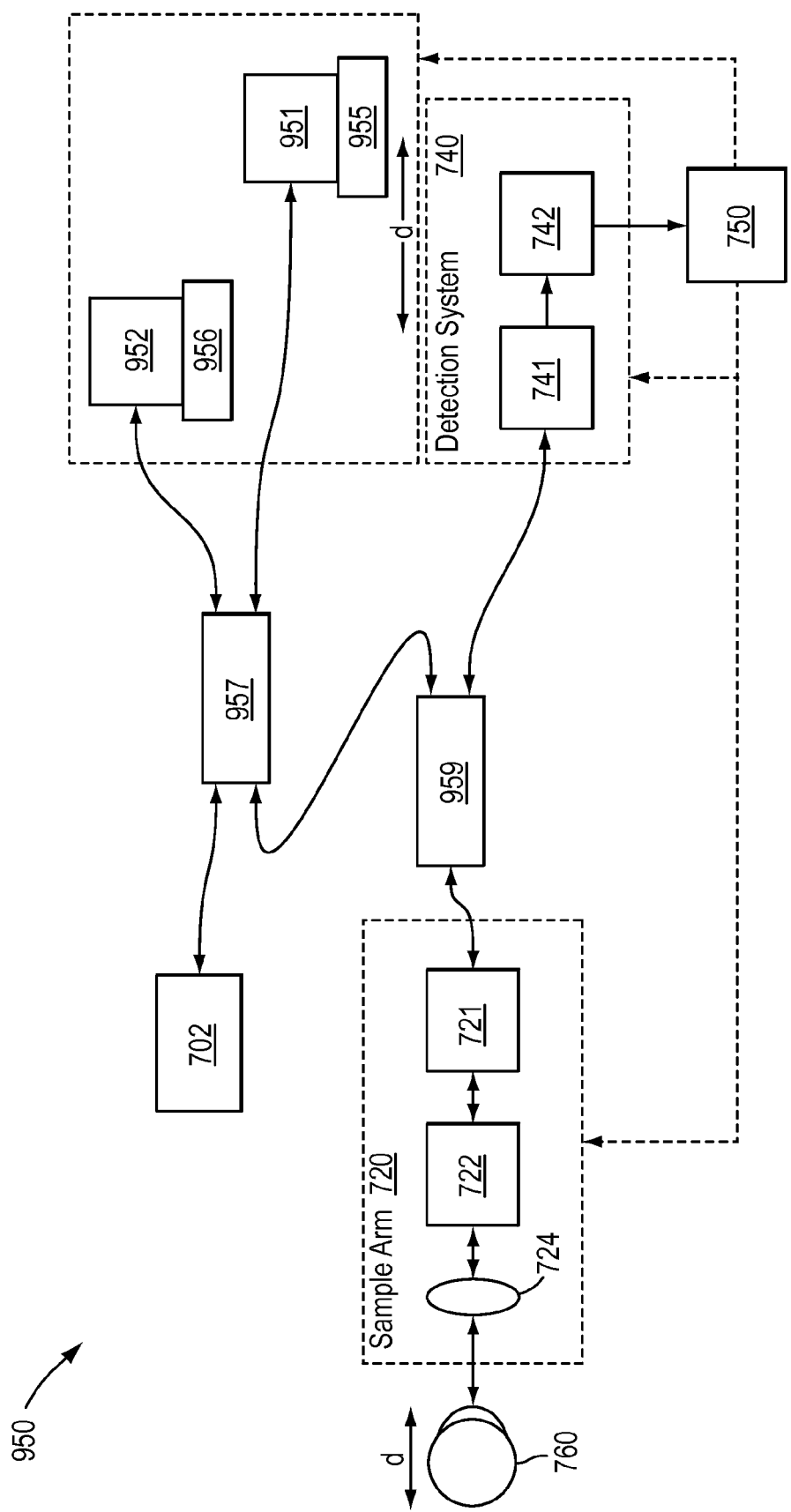

FIGS. 9A, 9B, and 9C illustrate some further embodiments of the invention.

Figure 10:
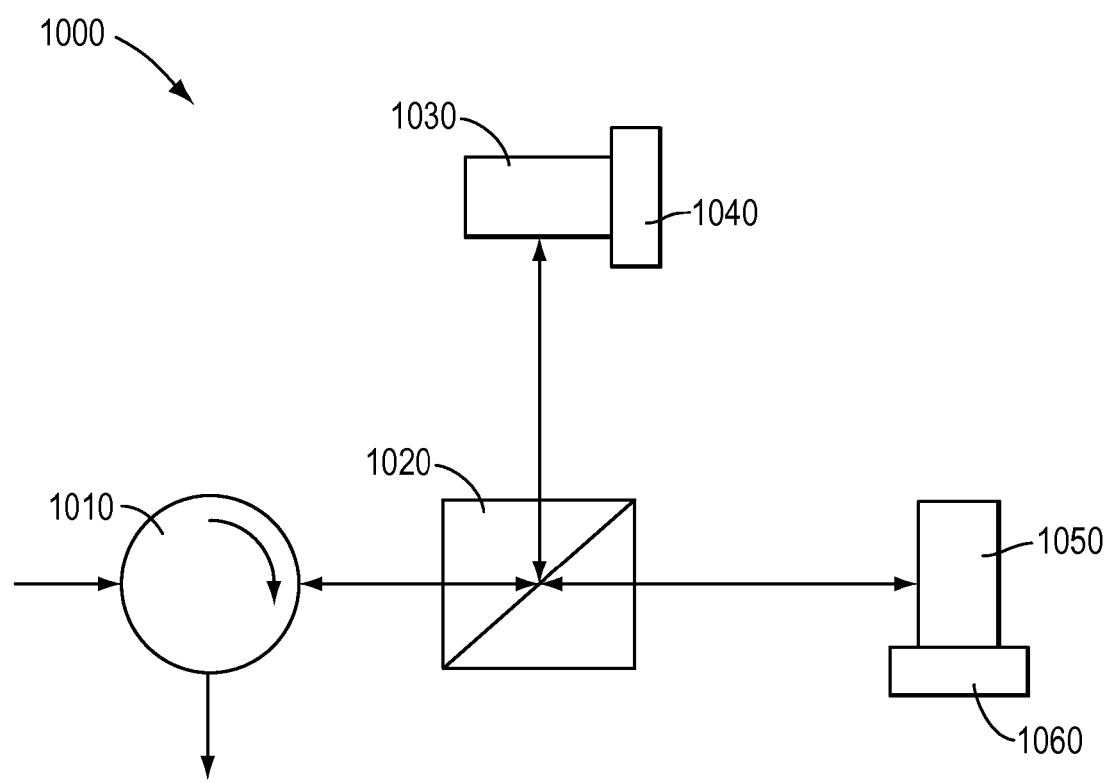

FIG. 10 illustrates an embodiment of an interferometer that may be utilized in some embodiments of the invention.

In the figures, elements having the same designation have the same or similar function.

DETAILED DESCRIPTION

A new branch of OCT technology based on Fourier-domain (FD-OCT) or Spectral-Domain OCT principles has been emerging. See M. Wojtkowski, R. Leitgeb, A. Kowalczyk, T. Bajraszewski, and A. F. Fercher, "In vivo human retinal imaging by Fourier domain optical coherence tomography," J. Biomed. Opt. 7, 457-463 (2002). FD-OCT provides significant signal-to-noise and speed improvements over previous time-domain OCT systems. See R. Leitgeb, C. K. Hitzenberger, and A. F. Fercher, "Performance of fourier domain vs. time domain optical coherence tomography," Opt. Express 11, 889-894 (2003); J. F. de Boer, B. Cense, B. H. Park, M. C. Pierce, G. J. Tearney, and B. E. Bouma, "Improved signal-to-noise ratio in spectral-domain compared with time-domain optical coherence tomography," Opt. Lett. 28, 2067-2069 (2003); and M. A. Choma, M. V. Sarunic, C. H. Yang, and J. A. Izatt, "Sensitivity advantage of swept source and Fourier domain optical coherence tomography," Opt. Express 11, 2183-2189 (2003). However, the signal-to-noise performance in FD-OCT decreases with increasing scan depth, which typically limits the scan range in FD-OCT to about 2 to 3 millimeters. To increase the scan depth range, phase shifting methods may be introduced to achieve full-range FD-OCT. Full-range complex FD-OCT uses phase shifting methods to resolve the ambiguity between negative and positive optical path differences with respect to the reference mirror in order to recover the full useful imaging range. See M. Wojtkowski, A. Kowalczyk, R. Leitgeb, and A. F. Fercher, "Full range complex spectral optical coherence tomography technique in eye imaging," Opt. Lett. 27, 1415-1417 (2002). Many other phase shifting mechanisms and algorithms have also been introduced to realize full range complex FD-OCT. See, e.g., Y. Yasuno, S. Makita, T. Endo, G. Aoki, M. Itoh, and T. Yatagai, "Simultaneous B-M-mode scanning method for real-time full-range Fourier domain optical coherence tomography," Appl. Opt. 45, 1861-1865 (2006) ("Yasuno"); R. K. Wang, "In vivo full range complex Fourier domain optical coherence tomography," Appl. Phys. Lett. 90, 054103 (2007) ("Wang"); and B. Baumann, M. Pircher, E. Gotzinger, and C. K. Hitzenberger, "Full range complex spectral domain optical coherence tomography without additional phase shifters," Opt. Express 15, 13375-13387 (2007) ("Baumann"). However, these methods can only increase the scan depth range of FD-OCT a limited amount, for example to about 4 to 6 millimeters.

Figure 1:
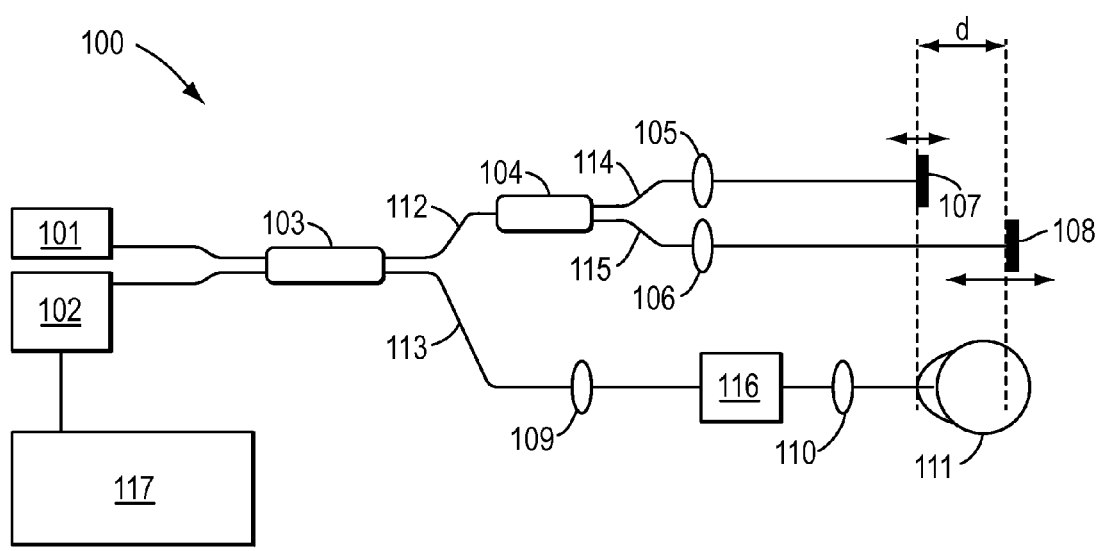
FIG. 1 shows a conventional OCT apparatus.

FIG. 1 illustrates a conventional OCT apparatus 100 for simultaneous acquisition of images. OCT apparatus 100 can either be of the time-domain or Fourier-domain OCT variety. See B. Grajciar, M. Pircher, C. K. Hitzenberger, O. Findl, and A. F. Fercher, "High sensitive measurement of the human axial eye length in vivo with Fourier domain low coherence interferometry," Opt. Express 16, 2405-2414 (2008). OCT Apparatus 100 can also be applied to both sweep-source based and spectrometer-based Fourier-domain OCT.

As shown in FIG. 1, OCT apparatus 100 includes a light source 101 coupled to provide light to a splitter/coupler 103. Splitter/coupler 103 provides light to a sample arm 113 and a reference arm 112. Light source 101 can be any light source that is suitable for the purpose of OCT imaging. A suitable light source that may be used in time-domain OCT or Fourier-domain OCT includes, but is not limited to, a broadband light source such as a superluminescent diode. A suitable light source that can be utilized in a swept-source version of Fourier-domain OCT includes, but is not limited to, a tunable laser source. In some embodiments, light source 101 may generate different wavelengths or different bandwidths for performing imaging at different tissue penetration and/or axial resolution.

Splitter/coupler 103 receives light from optical source 101 and sends the energy into both sample arm 113 and reference arm 112. As shown in FIG. 1, sample arm 113 may include various collimating lenses 109 and focusing lenses 110. Additionally, sample arm 113 includes a beam scanning mechanism 116 to direct the beam to perform two- or three-dimension transverse beam scanning and imaging of a sample 111. For achieving simultaneous imaging, reference arm 112 includes an additional splitter/coupler 104 that separates the beam of light received from splitter/coupler 103 into two or more reference arm paths, reference path 114 and reference path 115. Reference path 114 includes collimating lenses 105 and mirror 107. Reference path 115 includes collimating lenses 106 and mirror 108. Collimator lenses 105 and 106 in reference paths 114 and 115, respectively, collimate the beam from an optical fiber coupled to splitter/coupler 104 and focuses the beams back into the optical fiber after it is reflected from reference mirrors 107 and 108, respectively.

Reference mirrors 107 and 108 can be utilized to perform depth scans in the time-domain OCT, or can remain stationary in a Fourier-domain OCT process. The position of reference mirrors 107 and 108 can be adjusted to reflect the different axial scanning region of interest. In the example shown in FIG. 1, reference mirror 107 is adjusted to correspond with the anterior segment of the eye while reference mirror 108 is adjusted to correspond with the posterior segment of the eye. Therefore, as shown in FIG. 1, simultaneous images from the anterior and posterior segments of the human eye can be obtained.

The beams returning from the sample arm 113 and reference arm 112 are combined in splitter/coupler 103 and transmitted to detection system 102. Detection system 102 can be a spectrometer in spectrometer based Fourier-Domain OCT or a photo-diode detector system in swept-source based Fourier-domain OCT. The detected signal can then be sent to a processor 117, which is typically a computer system with sufficient data storage capabilities to hold the received image data.

As shown in FIG. 1, in order to acquire OCT images spanning different axial ranges, two reference mirrors (reference mirrors 107 and 108) with different reference arm lengths are simultaneously used. Each reference arm corresponds to a different depth position in the sample and both OCT images are detected simultaneously by a single detection system 102. However, in the technique illustrated in FIG. 1, any overlap of the OCT images will prevent the interpretation of the summed image since all the images are detected simultaneously and there is no information on how to separate the contributions from each of reference mirrors 107 and 108. Therefore, this method is limited to two reference mirrors and can only be used to image very simple samples with images that do not overlap or be used to acquire single-line OCT measurements (LCI measurements) with signals that also do not overlap.

Figure 2A:
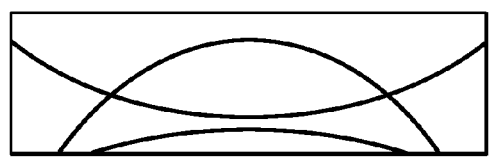
FIG. 2A shows an example of imaging results that may be achieved from the conventional OCT apparatus shown in FIG. 1.

FIG. 2A illustrates the typical result obtained with OCT apparatus 100 shown in FIG. 1. Since two reference arms, reference arms 114 and 115, are used in the system depicted in FIG. 1, the detection system 102 will simultaneously detect and acquire signals arriving from two different axial scanning regions of interest. FIG. 2A illustrates images from anterior and posterior segments of the human eye, as illustrated by the positioning of mirrors 107 and 108 of FIG. 1. However, as shown in FIG. 2A, the drawback with this technique is that the simultaneously detected signals can not be distinguished from each other and will both appear as overlapping images in the displayed image. The overlapping images shown in FIG. 2A diminish the interpretability of the resultant image and prevent unambiguous measurements between the signals arising from two different axial scanning regions of interest.

Figure 2B:
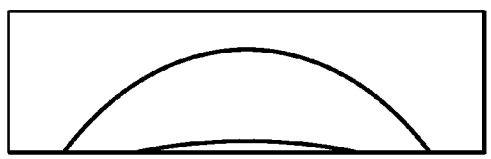
FIGS. 2B and 2C show an example of imaging results that may be achieved utilizing some embodiments of an OCT apparatus according to the present invention.
Figure 2C:

FIGS. 2B and 2C illustrate separated images of the posterior and anterior portion of the eye, respectively. FIGS. 2B and 2C illustrate the results obtained by some embodiments of the present invention. Some embodiments of the present invention provide a way to distinguish the simultaneously acquired signals and are able to separate the signals arising from two axial scanning regions of interest into two independent images. As mentioned above, separating the images removes the problems of interpretability arising from overlapping images. Additionally, some embodiments of the present invention allow for simultaneous acquisition of images, which allows for precise images arising from two different axial scanning regions of interest.

Some OCT imaging systems, as described for example in U.S. Pat. No. 7,400,410, include two separate OCT imagers operating at different optical wavelengths, which can be combined to simultaneously receive separate images from a single sample. Although this technique allows for the separation of two simultaneously acquired images, each of which may be set to measure images from differing depths, it also requires two separate OCT imagers. Multiple OCT imagers can significantly increase the complexity and the cost of the imaging system.

Separation of images as shown in FIG. 2B may be accomplished by substituting a switch for beamsplitter/coupler 104 in FIG. 1. However, even if a high-speed optical switching device is utilized, the two separated images will not be simultaneous. Simultaneous images can only be approximated if the switching speed of the optical switching device starts to approach zero. However, if the signals are not acquired simultaneously, then they are not registered one to the other and therefore the images are less valuable.

In accordance with some embodiments of the present invention, a method that can simultaneously acquire multiple OCT images spanning multiple axial ranges is presented. Under those circumstances, accurate registration in both the axial and transverse dimensions across all OCT images can be achieved and large scan-depth imaging or accurate morphometric measurements across large distances can be performed. In some embodiments of the present invention, the detection system only reads the images once and the resulting images can be precisely registered in both the axial and transverse dimensions. Further, some embodiments according to the present invention can be associated with an optical scanner that is used for non-invasive eye anatomy measurement, an optical imaging system for anterior chamber imaging, and/or an optical imaging system for posterior segment imaging.

Figure 3:
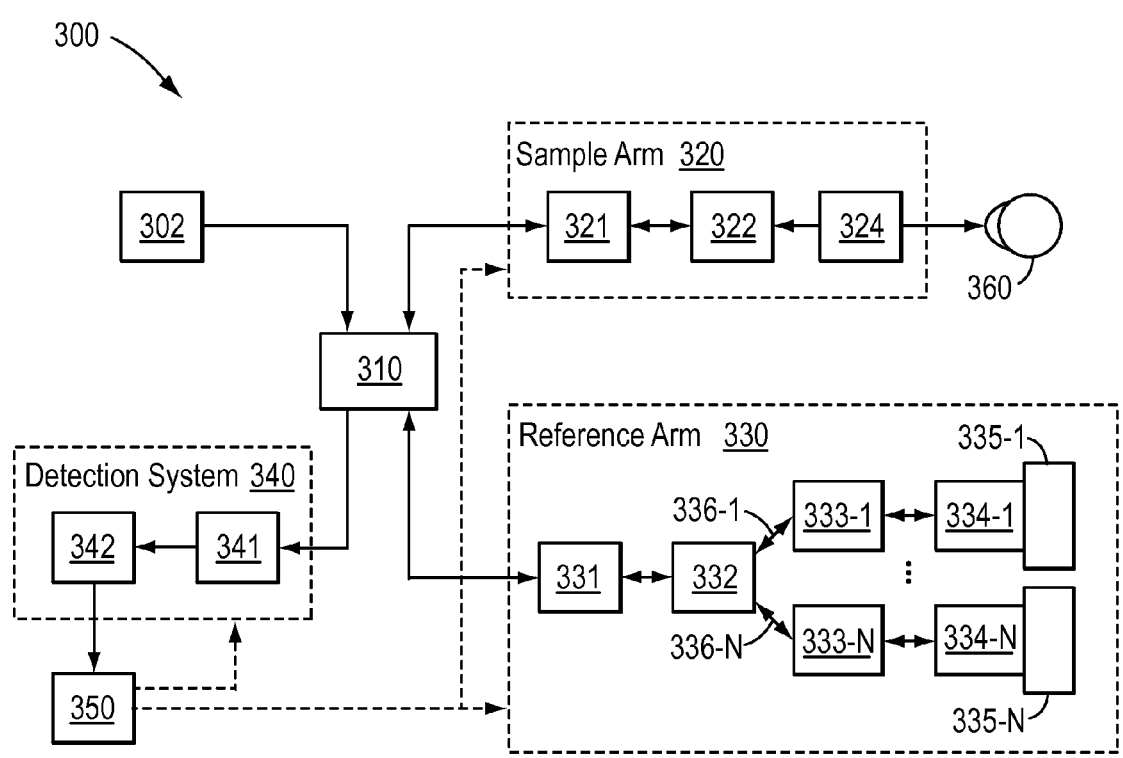
FIG. 3 shows an OCT system according to some embodiments of the present invention.

FIG. 3 illustrates an imager 300 according to some embodiments of the present invention. Imager 300 includes a light source 302 that may be chosen appropriately for either a swept-source or a spectrometer based Fourier-domain OCT procedure. As such, light source 302 may comprise any light source suitable for the purpose of OCT imaging. A suitable light source for the purpose of Fourier-domain OCT may include, but is not limited to, a broadband light source such as a superluminescent diode. A suitable light source for the purpose of achieving the swept-source version of Fourier-domain OCT may include, but is not limited to, a tunable laser source. In various embodiments, light source 302 may produce radiation at different wavelengths or with different bandwidths for performing imaging at different tissue penetration and/or axial resolution.

As shown in FIG. 3, light from light source 302 is directed to a light coupler 310, which sends energy from light source 302 into a sample arm 320 and a reference arm 330. Light coupler 310 of FIG. 3 can be a splitter/coupler that receives light from light source 302 and directs it to both sample arm 320 and reference arm 330, and receives light from sample arm 320 and reference arm 330 and directs the combined light beam to detection system 340. Sample arm 320 can include optics including collimating optics 321, beam scanning 322, and focusing optics 324. Beam scanning mechanism 322 may direct a light beam received from light coupler 310 to perform two- or three-dimension transverse beam scanning and imaging of sample 360. In some embodiments, collimating optics 321 may additionally include polarization controllers, which may be utilized in some embodiments to more precisely detect data resulting in an image. Sample arm 320 then provides the backscattered light from sample 360 to light coupler 310.

Reference arm 330 receives light from light source 302 through light coupler 310 and provides reference light to light coupler 310. Reference light from reference arm 330 is combined with backscattered light from sample arm 320 to produce spectral interference that can be detected by a detection system 340.

As shown in FIG. 3, reference arm 330 may include polarization controller 331 to assist in maximizing the interference fringe contrast detected by detection system 340. The reference arm may have one or more splitter/couplers 332 to further separate the reference beam into two or more reference paths for simultaneous detection. Reference paths 336-1 through 336-N are specifically shown in FIG. 3, where N can be any number of reference arms. In general, the number of separate reference paths N will be the number of separate image depths of interest.

Each of reference paths 336-1 through 336-N includes various optics 333-1 through 333-N as well as reference mirrors 334-1 through 334-N, respectively, for reflecting the energy from the light source 302 to provide the reference light. The optics 333-1 through 333-N in reference arm 330 may be used to collimate the beams from splitter/coupler 332 and couple the beams back into splitter/coupler 332 when they are reflected back from reference mirrors 334-1 through 334-N, respectively. In some embodiments, splitter/coupler 332 can be coupled to optics 333-1 through 333-N with optical fiber. Optics 333-1 through 333-N may include, but are not limited to, various collimating lenses suitable for this purpose.

As has been reported, for example, in Yasuno, Wang, and Baumann, a carrier frequency can be introduced into the spatial spectrograms by introducing a constant phase modulation in the reference and/or sample arm across the transverse scan. Such a modulation is typically utilized to double the conventional imaging range of a single reference arm OCT imager.

In accordance with some embodiments of the invention, reference beams returning from different reference paths include encoded information by utilizing different modulations into each of reference paths 336-1 through 336-N. Mirrors 334-1 through 334-N may be stationary or may be modulated by modulators 335-1 through 335-N, respectively. Modulation of reference mirrors 334-1 through 334-N during the transverse scanning of the sample may be equivalent to frequency modulation of the detected signal at detection system 340. As discussed above, it is therefore possible to encode information on the reference beams returning from different reference paths by using different phase modulations on each of reference mirrors 334-1 through 334-N.

Various methods may be enlisted in modulators 335-1 through 335-N to introduce a constant phase modulation into the reflected light beam from each of mirrors 334-1 through 334-N, respectively. In various embodiments, modulators 335-1 through 335-N may be a linear piezo-translation stage onto which mirrors 334-1 through 334-N, respectively, are mounted. The piezo-translation stage may be configured to move mirrors 334-1 through 334-N at some constant velocity across a transverse scan in the x or y direction (B-scan). In some embodiments, the phase modulation may be achieved in the sample arm scanning mechanism 322 by introducing an offset from the pivot point of scanner 321, as discussed in Baumann. In some embodiments, a grating-based phase delay line can be placed in reference arm 330 such that the optical group delay can be close to zero and only phase modulation is achieved. Another exemplary embodiment is shown in FIGS. 4A and 4B, which can also achieve phase modulation with nearly zero group delay.

The beams returning from sample arm 320 and reference arm 330 can be combined in coupler 310 and sent to detection system 340. Detection system 340 includes a detector 342 and optical components 341. Detector 342 can be a spectrometer in a spectrometer based Fourier-Domain OCT or a photo-diode detector system in a swept-source based Fourier-domain OCT. Optical components 341 may include appropriate optics to focus the beam from light coupler 310 onto detector 342. The detected signal is sent to a processor 350, which is typically a computer operating software to analyze the signals received from detector 342, store the data, and present the results in an appropriate fashion. Since the phase modulation in the reference arm may be synchronized to the transverse scanning performed in the sample arm, in some embodiments processor 350 may also send control and synchronization signals to sample arm 320, to reference arm 330, and to detection system 340 (dashed arrows).

Figure 4A:
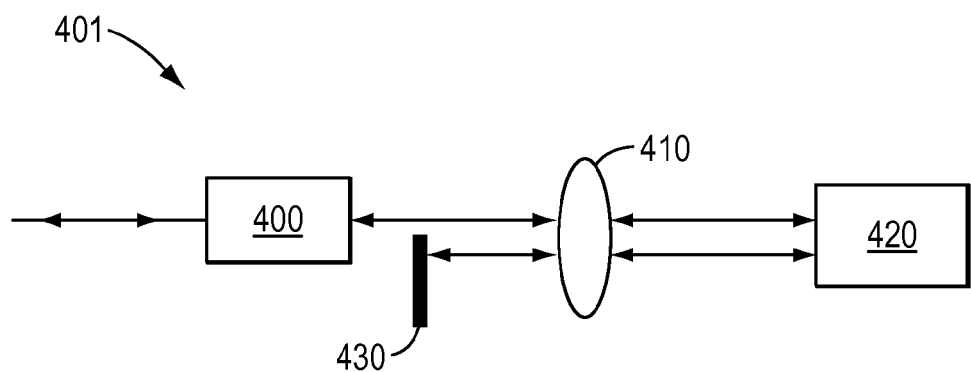
FIGS. 4A and 4B show embodiments of phase-scanning mechanisms that may be utilized in some embodiments of the present invention.
Figure 4B:
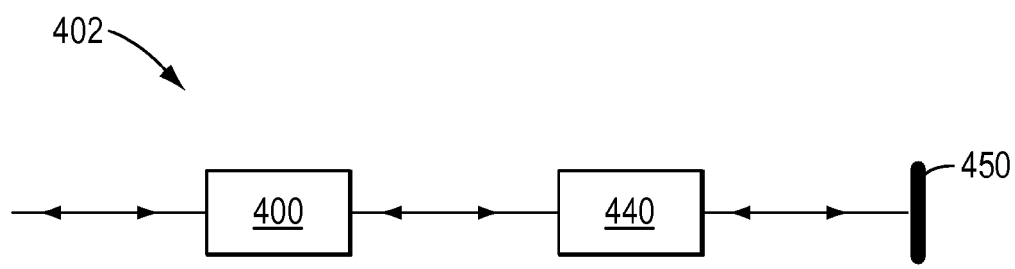

FIGS. 4A and 4B illustrate exemplary embodiments of modulation apparatus 401 and 402, respectively, suitable to achieve constant phase modulation in the reference arm. Each of apparatus 401 and 402 can be utilized in place of a mirror 334-$j$ and modulator 335-$j$ pair, where mirror 334-$j$ is an arbitrary one of mirrors 334-1 through 334-N and modulator 335-$j$ is a corresponding arbitrary one of modulators 335-1 through 335-N, and corresponds to the mirror and modulator in reference path 336$j$.

Apparatus 401 shown in FIG. 4A illustrates a double-pass configuration utilizing a galvanometer scanner 420 to achieve constant phase modulation in reference arm 330. In apparatus 401, the input beam may enter into collimating optics 400 and pass through a lens system 410 that focuses the beam to a mirror mounted on a galvanometer scanner 420. The beam hits the galvanometer mirror at an offset from the pivot point which will introduce phase modulation as the galvanometer mirror of galvanometer scanner 420 is rotated. In galvanometer 420, the galvanometer mirror is mounted at the focal plane of lens 410 and reflects the beam back through lens 410 to finally reach a retro-reflector 430, which can be a mirror. The returning beam from reflector 430 passes through lens 410, hits the galvanometer mirror of galvanometer scanner 420 again, and returns to the input through lens 410 and collimating optics 400. Because the galvanometer mirror of galvanometer scanner 420 is located at the back focal plane of lens 410, the beam reflected back from reflector 430 will return to the input of collimating optics 400 following the incident path, which is a double-pass configuration.

Apparatus 402 shown in FIG. 4B illustrates another exemplary embodiment of an apparatus suitable to achieve constant phase modulation. In apparatus 402, the input beam may enter into collimating optics 400 and passes through a phase modulation system 440 that can change the optical path length of the reference beam. An exemplary embodiment of phase modulation system 440 is an optical window mounted on a galvanometer scanner inserted into the reference beam path. As the galvanometer is rotated, the optical window changes angle with respect to the reference beam and the optical path length is changed. The beam passing through the phase modulation system continues to reach a retro-reflector 450, which may be a mirror. The returning beam from reflector 450 can go back through phase modulation system 440 before returning to the collimating optics 400 again to be coupled out of apparatus 402.

Figure 5A:
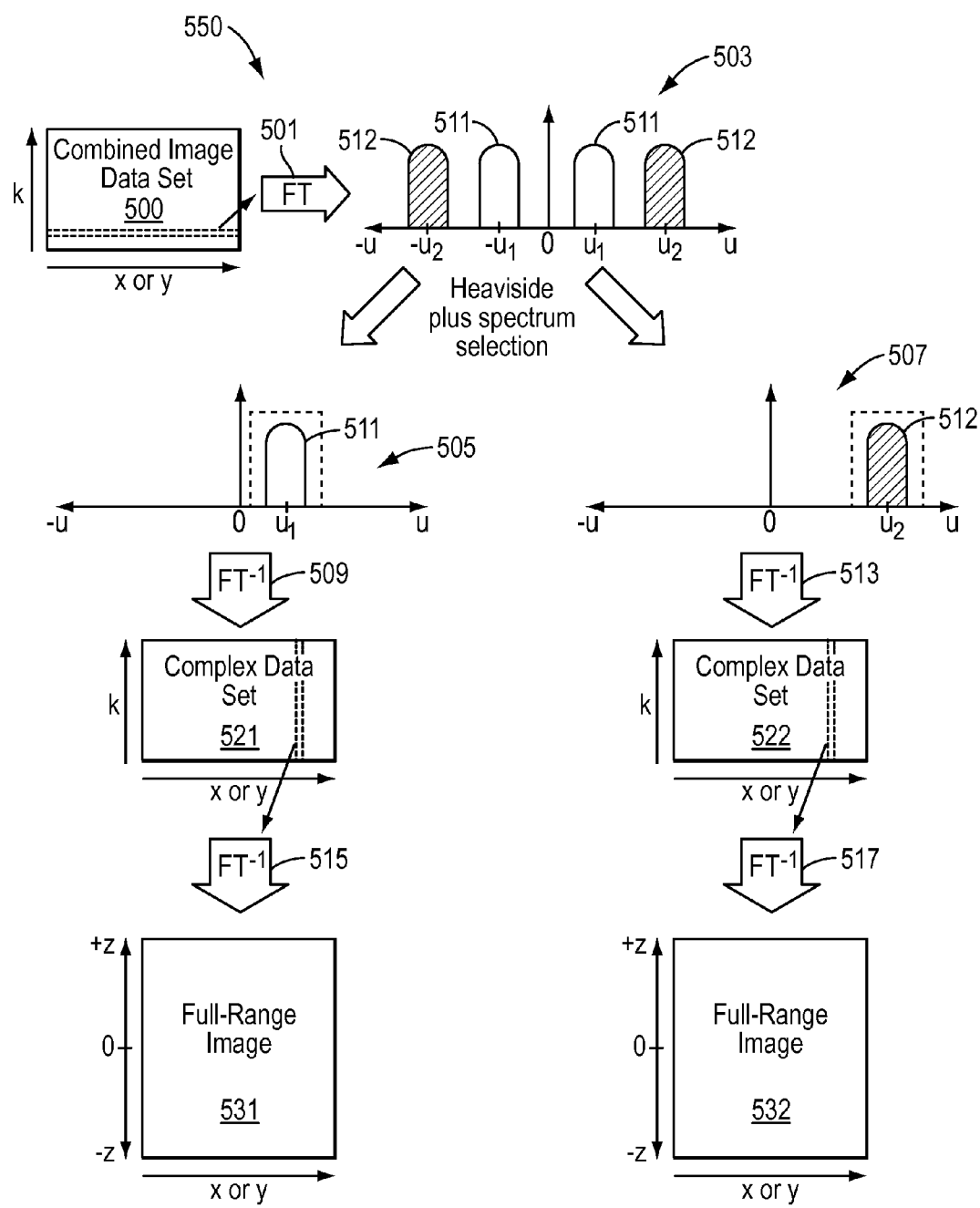
FIGS. 5A and 5B illustrate an embodiment of a signal processing procedure that may be utilized in some embodiments of the present invention.
Figure 5B:
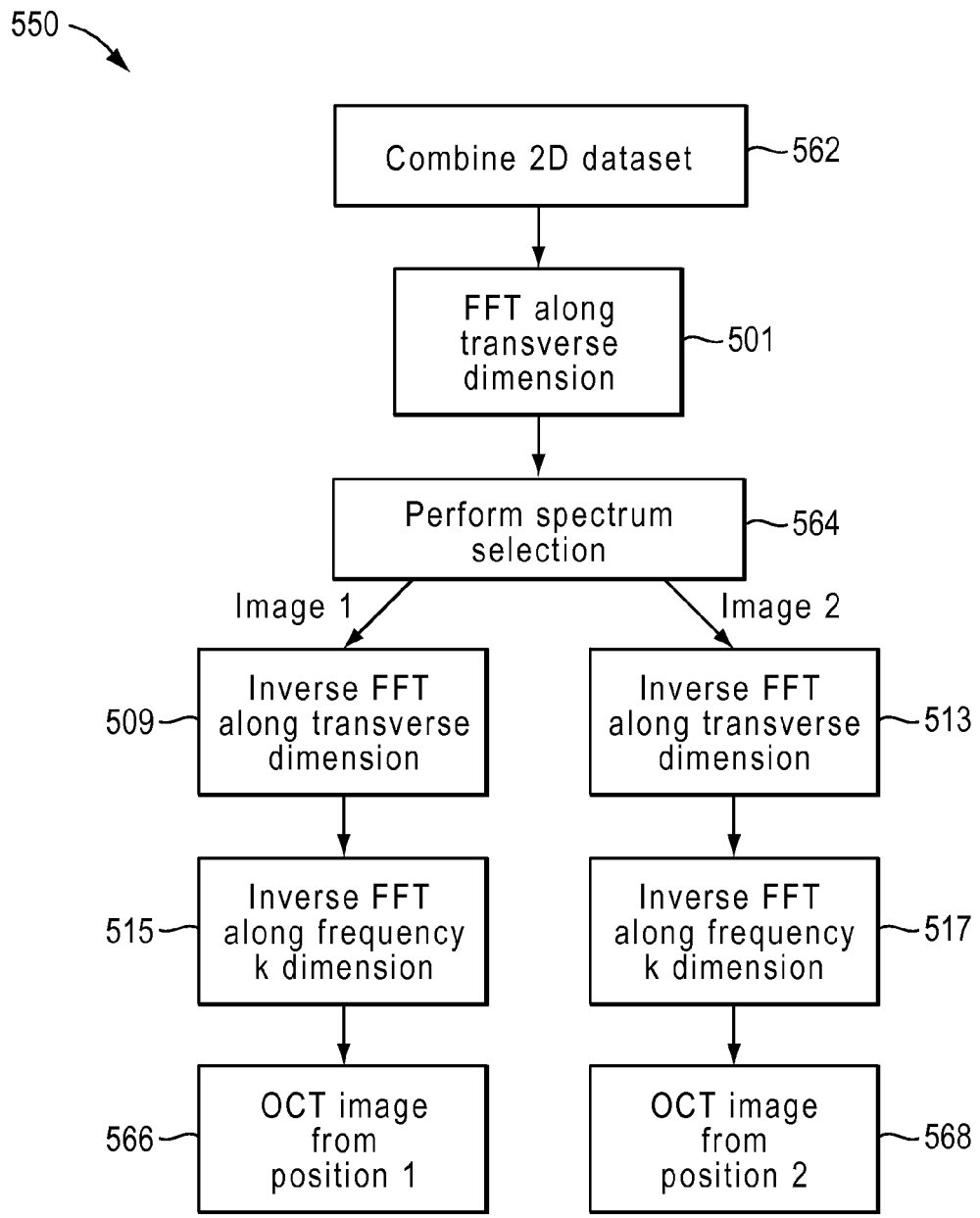

FIGS. 5A and 5B illustrate an exemplary embodiment of signal processing technique 550 that may be executed by processor 350 to distinguish the simultaneously acquired images. FIG. 5A illustrates the resulting data sets while FIG. 5B illustrates a flow chart of the data processing procedure that may be executed on processor 350. By using different phase modulation on each of reference arm paths 336-1 through 336-N, different carrier frequency can be induced into the spatial spectrograms corresponding to each of reference arm paths 336-1 through 336-N. Further, by arranging for different path lengths in each of reference arm paths 336-1 through 336-N, a plurality of images corresponding to different depths in sample 360 can be obtained.

For the illustrative purpose of FIGS. 5A and 5B, assume that a constant phase modulation is applied to modulator 335-1 such that the carrier frequency has a spatial frequency of $u_1$ in the transverse Fourier space. Furthermore, assume a constant phase modulation is applied to modulators 335-2 such that the carrier frequency has a spatial frequency of $u_2$ in the transverse Fourier space. If $u_1$ is sufficiently separated from $u_2$ in the transverse Fourier space, it will be possible to distinguish signals that are simultaneously acquired as illustrated in FIG. 5A. Although only reference paths 336-1 and 336-2 are illustrated here, one skilled in the art will readily recognize how to extend this to any number of reference paths 336-1 through 336-N in order to separate the images from each of the reference paths 336-1 through 336-N.

In step 562 of FIG. 5B, a combined dataset 500, as shown in FIG. 5A, is acquired. The spatial spectrograms from different ones of reference arm paths 336-1 through 336-N are detected simultaneously by detector 342 and stored in combined image data set 500. The combined image data set 500 contains the image data from all reference arm paths 336-1 through 336-N, of which the data from reference arm paths 336-1 and 336-2 are illustrated here. The detected data set may be a two-dimensional data set that has a dimension in spatial frequency k (or may be in wavelength γ before conversion to k). Another dimension will be in transverse position x or y depending on the scanning pattern and coordinate definition. In some embodiments, this second dimension can also simply be acquisition time when no transverse scanning is performed in the sample arm. In conventional FD-OCT, an inverse Fourier transform is performed along the k-dimension for every transverse position x or y, which yields the OCT signals for each transverse position.

In processing the simultaneously acquired images stored in combined data set 500, a Fourier transform 501 is performed along the transverse (x or y) dimension for every value in the k dimension. Due to the carrier frequencies $u_1$ and $u_2$ introduced by modulators 335-1 through 335-N, respectively, the frequency content associated with reference mirrors 334-1 through 334-N, respectively, will be centered at different carrier frequencies in the transverse Fourier space, as is shown in frequency distribution 503 of FIG. 5A. As shown in frequency distribution 503, the frequency content 511 centered on carrier frequency $\pm u_1$ contains information on the spatial spectrograms from reference arm mirror 334-1. The frequency content 512 centered on carrier frequency $\pm u_2$ contains information on the spatial spectrograms from reference arm mirror 334-2. In general, each of reference arms 336-1 through 336-N is centered at different frequency $u_1$ through $u_N$ in frequency distribution 503. If $u_1$ is sufficiently separated from $u_2$ in the transverse Fourier space, the information from different reference mirrors can be selected in spectrum selection step 564 by using Frequency filters. In some embodiments, in order to perform full range complex FD-OCT, only the spectra in the positive Fourier space is selected (i.e., applying a Heaviside function before spectrum selection) as illustrated by filters 505 and 507. As is illustrated in FIG. 5A, frequency content 511 can be separated from frequency content 512.

Applying an inverse Fourier transform 509 to filtered spectrum 511, complex data set 521 can be generated. Applying an inverse Fourier transform 513 to filtered spectrum 512, complex data set 522 can be generated. In general, an inverse Fourier transform can be applied to each of the separated spectra formed in spectrum selection 564. As discussed above, a complex data set such as complex data sets 521 and 522 can then be generated for each of reference paths 336-1 through 336-N.

Complex data set 521 shown in FIG. 5A corresponds to the spatial spectrogram from reference mirror 334-1 and complex data set 522 corresponds to the spatial spectrogram from reference mirror 334-2. Through the appropriate selection of phase modulations on modulators 335-1 and 335-2, it is therefore possible to distinguish simultaneously acquired signals.

The final step in the process to generate OCT images shown in the embodiment shown in FIGS. 5A and 5B is to perform inverse Fourier transform along the k-dimension for every transverse position x or y as in conventional FD-OCT. As shown in FIGS. 5A and 5B, inverse Fourier transform 515 is performed on complex data set 521 to form full-range image 531. Similarly, inverse Fourier transform 517 is performed on complex data set 522 to form full-range image 532. Because complex data sets 521 and 522 include both real and imaginary information, the complex conjugate mirror image will not be present and the full imaging range (+z to −z) of the FD-OCT system can be utilized. As shown in FIG. 5A, the full-range OCT image 531 corresponds to the image acquired from reference mirror 334-1 and the full-range OCT image 532 corresponds to the image acquired from reference mirror 334-2. By selecting appropriate optical path delays in the reference paths containing reference mirrors 334-1 and 334-2, it is then possible to simultaneously acquire images from different axial scanning regions of interest in the sample. In general, a full-range image can be obtained for each of reference paths 336-1 through 336-N.

Although FIGS. 5A and 5B show an example for two reference paths 336-1 and 336-2, as discussed above any number of reference paths 336-1 through 336-N can be utilized. Process 550 illustrated in FIGS. 5A and 5B can be applied generally to multiple reference mirrors such that multiple spatial spectrograms are detected simultaneously. As long as sufficient carrier frequencies can be selected such that there is no overlap of the frequency contents in the transverse Fourier space, all the simultaneously detected signals can be distinguished from each other.

In some embodiments, one of the carrier frequencies ($u_1$ for example) can be zero such that no phase modulation is performed in that reference arm path (i.e. a stationary mirror). This case will be the same as conventional FD-OCT and the full imaging range (+z to −z) will not be available. However, for imaging thin samples such as the retina, half of the full imaging range (positive-z or negative-z space) is often sufficient. As long as the second carrier frequency ($u_2$ for example) is sufficiently separated from $u_1$ (zero in this case) in the transverse Fourier space, it will be possible to distinguish signals that are simultaneously acquired from two different axial scanning regions of interest.

Figure 6A:
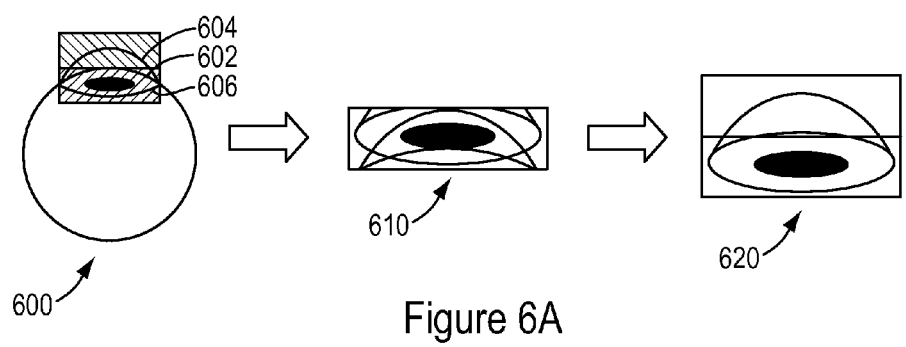
FIGS. 6A and 6B show exemplary utilization of some embodiments of the present invention to extend the imaging range inside human tissue.
Figure 6B:
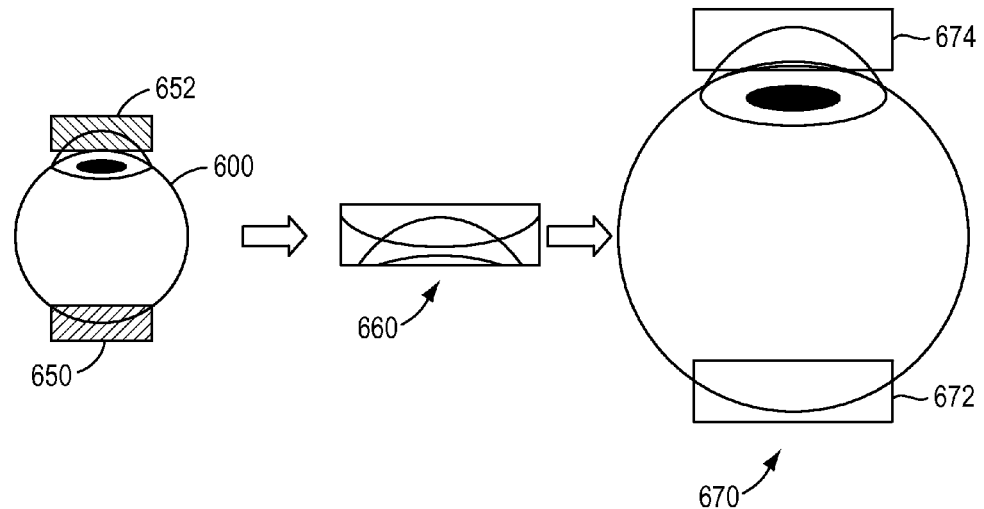

FIGS. 6A and 6B illustrate examples of utilizing embodiments of the present invention to extend the imaging range inside a sample such as the human eye. Because the images can be acquired simultaneously, precise registration can be achieved across both the axial and transverse dimensions. Therefore it is possible to extend the imaging range through precise calibration of the path length differences in reference paths 336-1 through 336-N. FIG. 6A shows an extended imaging range in the anterior segment of a human eye 600. As shown in FIG. 6A, scan range 602 can be performed. The maximum imaging range of full range complex FD-OCT is usually about 6 mm, which is not sufficient to imaging the entire anterior chamber including the posterior capsule of the lens. The example shown in FIG. 6A shows that the optical paths of two reference mirrors can be adjusted such that one reference mirror, for example reference mirror 334-1, images a front part 604 of the anterior chamber while a second reference mirror, for example reference mirror 334-2, images a back part 606 of the anterior chamber. Imaging region 602 corresponds to rectangular boxes with diagonal lines.

Using conventional prior art techniques, the simultaneously acquired images would overlap and render the resultant image, as is shown in image 610 in FIG. 6A, uninterpretable. In some embodiments of the present invention, the images acquired from the two separate axial scanning regions of interest can be distinguished and combined together to form one image 620 that effectively doubles the imaging range of the system to about 12 mm, sufficient to cover the entire anterior chamber of eye 600.

FIG. 6B shows an example of utilizing some embodiments of the present invention for performing simultaneous imaging at vastly different axial scanning regions of interest. As shown in FIG. 6B, imaging regions 650 and 652 are of interest in eye 600. The optical path in two reference mirrors can be adjusted such that one reference mirror, for example reference mirror 334-1, images the front part of the anterior chamber while the second reference mirror, for example reference mirror 334-2, images the retina in the posterior segment of the eye. Imaging regions 650 and 652 correspond to rectangular boxes with diagonal lines. Using conventional prior art techniques, the simultaneously acquired images would overlap and render the resultant image, shown as image 660 in FIG. 6B, uninterpretable. Image 670 illustrates separated images 672 and 674 acquired from the two separate axial scanning regions of interest. Because the optical path difference between the two reference mirrors 334-1 and 334-2 can be measured precisely, the separation distance between the two images 672 and 674 can be determined and the images can be placed in their correct anatomical relationship in the context of the entire imaging sample, such as the human eye 600. Furthermore, since the two images are acquired simultaneously, morphmetric measurements such as the distance from the front surface of the eye to the back surface of the eye can be precisely determined.

As discussed above, any number of separated images can be obtained. FIGS. 6A and 6B illustrate separation of two images from two reference paths. In some embodiments, the examples shown in FIGS. 6A and 6B can be combined through the use of three reference mirrors for simultaneous acquisition. It is therefore possible to perform imaging of the entire anterior chamber with about 12 mm of imaging range as shown in FIG. 6A while simultaneously acquiring an image of the retina in the posterior segment for morphometric measurements as shown in FIG. 6B.

Figure 7:
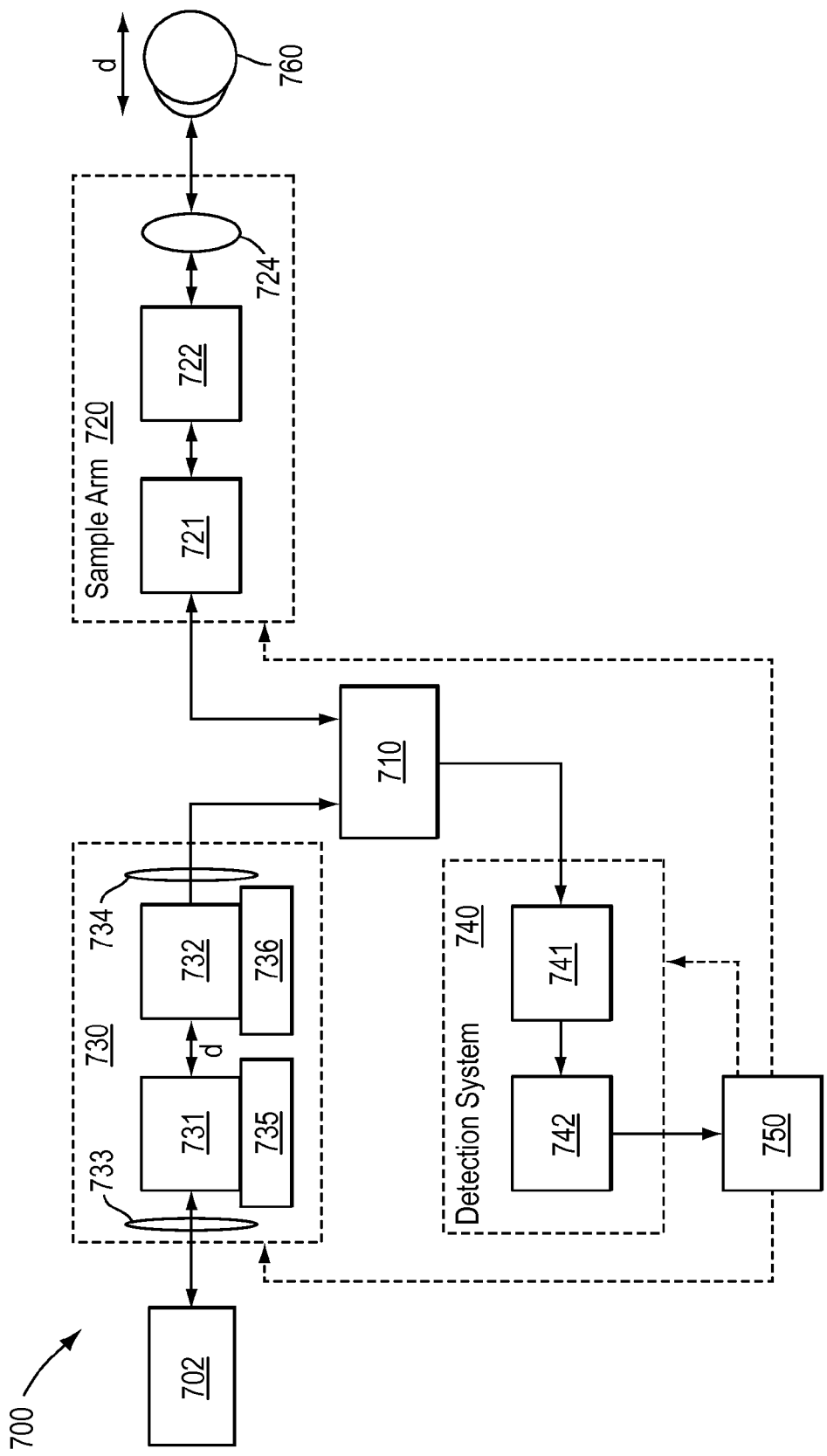
FIG. 7 illustrates another OCT system according to some embodiments of the present invention.

FIG. 7 illustrates an OCT imager 700 according to some embodiments of the present invention. OCT imager 700 represents a dual-beam low coherence interferometer. In some embodiments, OCT imager 700 is insensitive to the motion of the sample. In some embodiments, OCT imager 700 can be suitable for both swept-source and spectrometer based Fourier-domain low-coherence interferometry (LCI). In general, OCT imager 700 includes a light source 702, an interferometer 730, a sample arm 720, a detection system 740, and a processor 750. Light source 700 may include any light source suitable for the purpose of LCI or OCT imaging. A suitable light source for the purpose of Fourier-domain OCT may include, but is not limited to, a broadband light source such as a superluminescent diode. A suitable light source for the purpose of achieving the swept-source version of Fourier-domain OCT may include, but is not limited to, a tunable laser source. In some embodiments, light source 702 may contain different wavelengths or different bandwidths for performing imaging at different tissue penetration and/or axial resolution.

As shown in FIG. 7, interferometer 730 may include reflective surfaces 731 and 732 separated by an adjustable distance. The relative optical paths of the reflective surfaces 731 and 732 correspond with the separation in depth of the acquired images One or both of the two reflective surfaces may be modulated during the data acquisition by modulators 735 and 736 to provide a constant phase modulation to the detected signal during acquisition. Lens systems 733 and 734 couple light in and out of interferometer 730. Light from interferometer 730 is provided to light coupler 710, which directs light into sample arm 720 and directs light received from sample arm 720 to detection system 740. In some embodiments, light coupler 710 can be an optical circulator. In some embodiments, light coupler 710 can be a splitter/coupler. Sample arm 720 can include various collimating optics 721, a beam scanning mechanism 722, and focusing optics 724. Beam scanning mechanism 722 can direct the beam to perform two- or three-dimension transverse beam scanning and imaging of a sample 760, or it can remain stationary for axial measurements.

The distance d between the two reflective surfaces 731 and 732 can be adjusted to match the axial length of the eye. In such case, the low-coherence interferometry signal returning from both the cornea and the retina can be presented to the detection system 740. Detection system 740, as shown in FIG. 7, can include optics 741 and a detector 742. Detector 742 can be a spectrometer in spectrometer based Fourier-Domain OCT or a photo-detector system (e.g., a photo-diode detector system) in swept-source based Fourier-domain OCT. Appropriate optics or optical components 741 may be employed to focus the beam onto detector 742. Detector 742 provides a signal to processor 750 in response to the beam. Processor 750, which can be a computer system, stores the signal as image data and can process the image data as has been previously described. Since the phase modulation in the reference arm needs to be synchronized to the acquisition, the computer may also send control and synchronization signals to the sample arm, the reference arm, and/or the detection system (dashed arrows).

In some embodiments, one or both of reflective surfaces 731 and 732 of interferometer 730 may be modulated respectively by modulators 735 and 736 during data acquisition to provide a constant phase modulation. It is therefore possible to encode a phase modulation to the signal returning from the longer optical path length of the sample arm (e.g., the retina). This will allow separation of the signals returning from different path lengths in the sample (e.g., the cornea and the retina). Various methods may be enlisted in the modulators 735 and 736 to introduce a constant phase modulation to reflective surfaces 731 and 732. Another exemplary embodiment is shown in FIGS. 4A and 4B, which can be used to achieve constant phase modulation during data acquisition.

Figure 8:
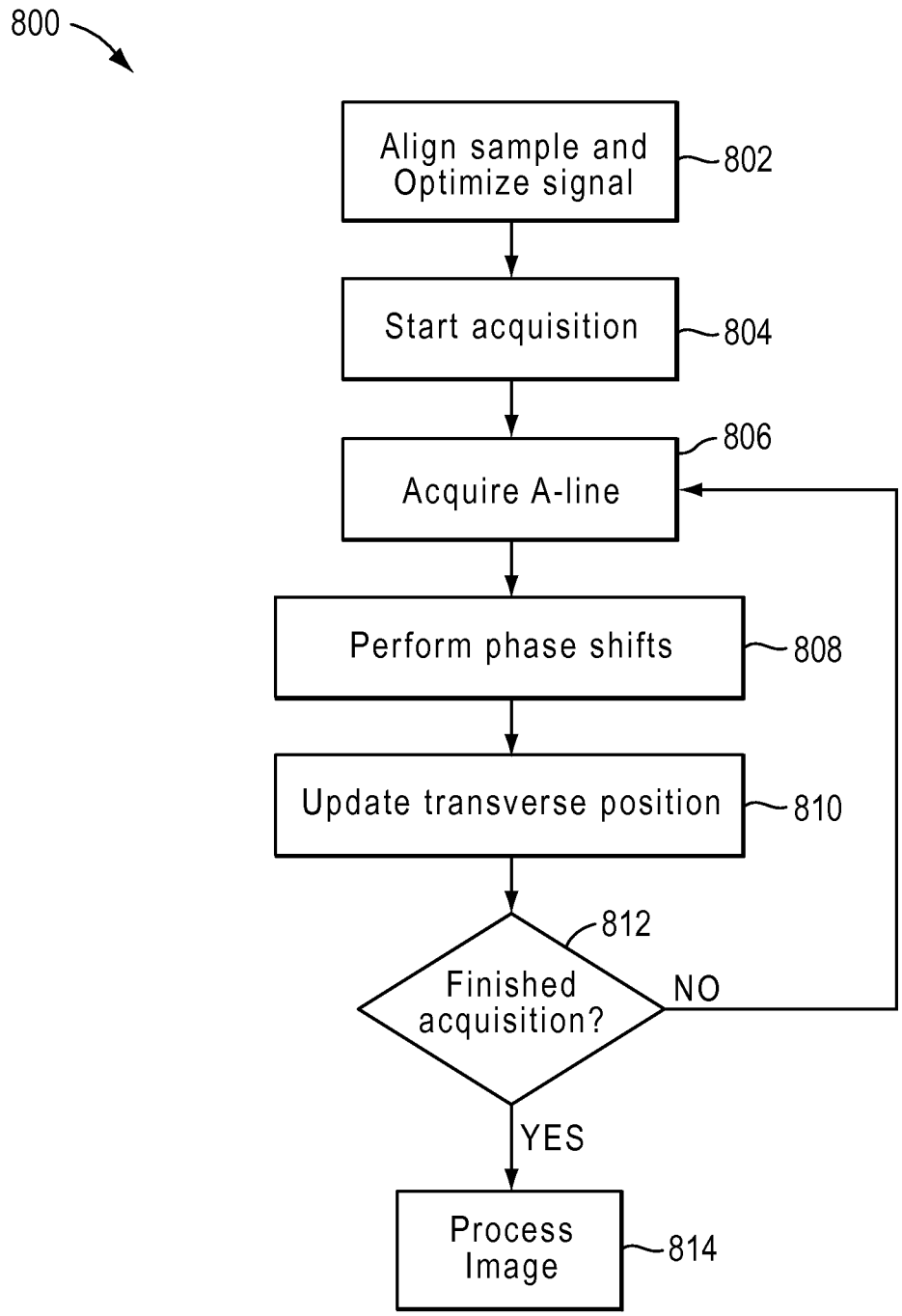
FIG. 8 illustrates a flow chart for acquiring images according to some embodiments of the present invention.

FIG. 8 illustrates a process 800 for providing images in an OCT imager according to some embodiments of the present invention. As shown in FIG. 8, first a sample, such as sample 360 shown in FIG. 3 or sample 760 shown in FIG. 7, is aligned with OCT imager in step 802 so that signal strength can be optimized. After alignment, in step 804 data acquisition is begun. In step 806, a line of data for an A-line scan is acquired. In step 808, phase shift modulation for the next line of data is performed. Phase shift modulations are detected, for example, in detection system 340 of the embodiment shown FIG. 3 or detection system 740 of the embodiment shown in FIG. 4. In step 810, the transverse position is changed. Changing transverse position can be accomplished, for example, by scan mechanism 322 in the embodiment shown in FIG. 3 or scan mechanism 722 in the embodiment shown in FIG. 7. In step 812, if the full scan is not yet completed then process 800 returns to step 806. If the full scan has been completed, then process 800 enters image processing 814. Image processing 814 can, for example, execute process 550 illustrated in FIGS. 5A and 5B.

FIG. 9A illustrates OCT imager 700 where light coupler 710 is implemented as circulator 910. Circulator 910 receives light from interferometer 730 and provides it to sample arm 720 and receives light from sample arm 720 and provides it to detector system 740. An advantage of circulator 910 over a splitter/coupler as light coupler 710 is the higher percentage of light coupled into sample arm 720 and detection system 740.

FIG. 9B illustrates imager 920, which represents another embodiment of an imager according to some embodiments of the present invention. Imager 920 includes light source 702, detection system 740, processor 750, and sample arm 720 as discussed with respect to imager 700 of FIG. 7. Light from light source 702 is coupled into sample arm 720 and interferometer 930 through splitter/coupler 925. Light received at splitter/coupler 925 from sample arm 720 and interferometer 930 is combined and coupled into detection system 740. As shown in FIG. 9B, interferometer 930 includes reflectors 931 and 932, each of which may be coupled to a modulator 935 and 936, respectively. As discussed with respect to FIG. 7, the distance between reflectors 931 and 932 corresponds with the difference in depth between images in sample 760. Lens systems 933 and 934 couple and focus light through interferometer 930. As shown in FIG. 9B, reflector 931 can be partially reflecting and reflector 932 can be fully reflecting.

FIG. 9C shows an imager 950, which illustrates another embodiment according to the present invention. As shown in FIG. 9C, light from source 702 is coupled into splitter/coupler 957, which transmits light to reflectors 951 and 952. Reflectors 951 and 952 may also include coupling optics to receive light from splitter/coupler 957 and couple light back into splitter/coupler 957. As shown in FIG. 9C, reflectors 951 and 952 may be coupled to modulators 955 and 956, respectively. Although only two reflectors, reflectors 951 and 952, are shown in FIG. 9C, additional splitters may be utilized to add as many reflectors, each providing a different modulated beam corresponding to a different image depth, as desired, which is similar to the embodiment shown in FIG. 3.

Light received from reflectors 951 and 952 is combined in splitter/coupler 957 and coupled into light coupler 959. Light coupler 959 can be a splitter/coupler or a circulator such as circulator 910 shown in FIG. 9A. As shown in FIG. 9C, Light from light coupler 959 is coupled into sample arm 720. Light received from sample arm 720 is received in light coupler 959 and transmitted into detection system 740. As before, processor 750 can be coupled to control aspects of imager 950.

FIGS. 7 and 9A illustrate interferometer 730, which includes two partially reflecting mirrors 731 and 732. FIG. 9B illustrates interferometer 930, which includes one partially reflecting mirror 931 and a fully reflecting mirror 932. FIG. 10 illustrates an interferometer 1000 that may be utilized in place of interferometer 930 of FIG. 9B or interferometer 730 of FIG. 7 or 9A.

As shown in FIG. 10, light enters interferometer 1000 in circulator 1010. In some embodiments, a splitter/coupler can be substituted for circulator 1010. Light from circulator 1010 enters beam splitter 1020, where it is split and coupled into reflectors 1030 and 1050. As discussed above, reflectors 1030 and 1050 may include coupling optics. Further, reflectors 1030 and 1050 are coupled to modulators 1040 and 1060, respectively. The difference in path length utilizing reflector 1030 and reflector 1050 corresponds with the different depth of image acquired.

In each of the embodiments, light may be coupled from one component to another in any fashion, for example with optical fiber. Further, some embodiments may include focusing or coupling optics in various positions, as needed.

For purposes of explanation, some embodiments of the invention are discussed above. One skilled in the art may recognize various alternatives from the embodiments disclosed. Such alternatives are intended to be within the scope of this disclosure. Further, these embodiments are not intended to be limiting on the scope of the invention. Therefore, the invention is limited only by the following claims.

We claim:

1. An imager, comprising:
   a light source;
   a light coupler;
   an interferometer disposed between the light source and the light coupler, the interferometer comprising:
     a first reflective surface and a first modulator configured to provide a first constant phase modulation to the first reflective surface, and
     a second reflective surface and a second modulator configured to provide a second constant phase modulation to the second reflective surface, the second reflective surface being separated from the first reflective surface by a distance,
   wherein:
     the distance between the first reflecting surface and the second reflecting surface corresponds to differing image depths in a sample;
   a sample arm coupled to the light coupler that receives light from the light source through the light coupler, directs the light to the sample, and captures light returning from the sample;
   a detector system configured to receive the captured light from the sample and the first and second constant phase modulations provided to the first and second reflective surfaces; and
   a processor that receives signals from the detector system and separates a plurality of images that overlap corresponding with the differing image depths in the sample.

2. The imager of claim 1, wherein the light coupler is a splitter/coupler.

3. The imager of claim 1, wherein the light coupler is a circulator.

4. The imager of claim 1, wherein the light coupler comprises a splitter/coupler that receives light from the light source, provides the light to the sample arm, combines light received from the sample arm and the interferometer, and provides light to the detector system.

5. The imager of claim 1, wherein the light coupler provides light to the sample arm from the interferometer and to the detector system from the sample arm.

6. The imager of claim 5, wherein the light coupler is a circulator.

7. The imager of claim 5, wherein the light coupler is a splitter/coupler.

8. The imager of claim 1, wherein the processor executes instructions to:
   simultaneously obtain a plurality of overlapping images from the detector system, the plurality of overlapping images corresponding to the differing image depths in the sample;
   combine the simultaneously obtained plurality of overlapping images into a combined dataset, the combined dataset having a spatial frequency dimension and a transverse dimension;
   perform a transform on the combined dataset along the transverse dimension for each value in the spatial frequency dimension to form a plurality of distributions along a carrier frequency dimension in the transformed dataset;
   separate the plurality of distributions into a plurality of spectra based on a carrier frequency of each of the plurality of spectra; and
   perform mathematical operations on each of the plurality of separated spectra to form a plurality of full-range images corresponding with the differing image depths in the sample.

9. The imager of claim 8, wherein the transform is a Fourier transform.

10. The imager of claim 8, wherein the mathematical operations include:
- an inverse Fourier transform to be performed on the separated spectra; and
- an inverse Fourier transform to be performed along a frequency dimension on the separated spectra.

11. The imager of claim 1, wherein the processor provides control signals to the interferometer and the sample arm.

12. The imager of claim 1, wherein the light source includes a broad band source and the detector system includes a spectrometer.

13. The imager of claim 1, wherein the light source includes a swept laser source and the detector system includes a photodiode detector system.

* * * * *